US011508477B2

United States Patent
Wang

(10) Patent No.: US 11,508,477 B2
(45) Date of Patent: Nov. 22, 2022

(54) SURGERY SYSTEM, CONTACTLESS CONTROL PANEL FOR SURGERY SYSTEM, AND CONTROL METHOD

(71) Applicant: TAIWAN MAIN ORTHOPAEDIC BIOTECHNOLOGY CO., LTD., Taichung (TW)

(72) Inventor: Min-Liang Wang, Taichung (TW)

(73) Assignee: Taiwan Main Orthopaedic Biotechnology Co., Ltd., Taichung (TW)

(*) Notice: Subject to any disclaimer, the term of this patent is extended or adjusted under 35 U.S.C. 154(b) by 198 days.

(21) Appl. No.: 16/918,065

(22) Filed: Jul. 1, 2020

(65) Prior Publication Data
US 2021/0225504 A1 Jul. 22, 2021

(30) Foreign Application Priority Data
Jan. 21, 2020 (TW) .................. 109102270

(51) Int. Cl.
*G16H 40/67* (2018.01)
*A61B 90/00* (2016.01)
(Continued)

(52) U.S. Cl.
CPC ............ *G16H 40/67* (2018.01); *A61B 90/361* (2016.02); *A61B 90/94* (2016.02); *G06T 11/00* (2013.01);
(Continued)

(58) Field of Classification Search
None
See application file for complete search history.

(56) References Cited

U.S. PATENT DOCUMENTS

2007/0300182 A1* 12/2007 Bilow .................. G06F 3/0425
  715/799
2013/0241832 A1* 9/2013 Rimon ................ G06F 3/03547
  345/158

FOREIGN PATENT DOCUMENTS

| CN | 1708764 A | 12/2005 |
| CN | 101401059 A | 4/2009 |
| CN | 101401059 B | 8/2012 |

OTHER PUBLICATIONS

Search Report appended to an Office Action, which was issued to Chinese counterpart application No. 202010185717.3 by the CNIPA dated Nov. 30, 2020, with an English translation thereof (6 pages including English translation).

(Continued)

*Primary Examiner* — Kyle Zhai
(74) *Attorney, Agent, or Firm* — Michael Best & Friedrich LLP

(57) ABSTRACT

A surgery system includes a contactless control panel, an infrared camera, a computer and a display. The contactless control panel includes control areas which are arranged in a predetermined pattern and are coated with infrared reflective material to reflect infrared radiation. The infrared camera captures an infrared image of the control areas. The computer performs image recognition on the infrared image, determines, based on the predetermined pattern stored in advance and a result of the image recognition, which one of the control areas is masked, and generates a device control signal based on a function corresponding to the one of the control areas that is determined to be masked. The display device displays images based on the device control signal.

4 Claims, 3 Drawing Sheets

(51) Int. Cl.
      *A61B 90/94*      (2016.01)
      *G16H 20/40*      (2018.01)
      *G16H 30/40*      (2018.01)
      *G06T 11/00*      (2006.01)
      *G06V 10/143*    (2022.01)
      *G06V 20/20*     (2022.01)

(52) U.S. Cl.
      CPC .......... *G06T 11/008* (2013.01); *G06V 10/143* (2022.01); *G06V 20/20* (2022.01); *G16H 20/40* (2018.01); *G16H 30/40* (2018.01); *A61B 2090/3762* (2016.02); *A61B 2090/397* (2016.02); *G06T 2210/41* (2013.01); *G06V 2201/03* (2022.01)

(56) References Cited

OTHER PUBLICATIONS

Search Report appended to an Office Action, which was issued to Taiwanese counterpart application No. 109102270 by the TIPO dated Jul. 9, 2020, with an English translation thereof (2 pages).

\* cited by examiner

SURGERY SYSTEM, CONTACTLESS CONTROL PANEL FOR SURGERY SYSTEM, AND CONTROL METHOD

CROSS-REFERENCE TO RELATED APPLICATION

This application claims priority of Taiwanese Invention Patent Application No. 109102270, filed on Jan. 21, 2020.

FIELD

The disclosure relates to a surgery system, a contactless control panel for a surgery system, and a control method.

BACKGROUND

A surgical navigation system with intra-operative real-time imaging assists a surgeon in precisely and safely locating a surgical target (e.g. a lesion) on a subject, or in placing an implant (e.g., electrodes for deep brain stimulation, DBS, or pedicle screws). Therefore, damage to surrounding tissues (e.g., important nervous tissues) may be avoided during surgery; size of surgical wounds may be reduced; success rate of surgeries may be increased; and postoperative recovery of subjects may be improved.

During surgery, the surgeon often needs assistants to help operate the surgical navigation system (e.g., toggle between images) because the surgeon has to keep his/her hands aseptic to prevent infection. However, teamwork between the surgeon and the assistants may sometimes be inefficient or ineffective because it is relatively difficult for the surgeon to clearly express the desired operations or for the assistants to correctly comprehend the surgeon's directions, and/or because of the lack of coordination between the surgeon and the assistants.

SUMMARY

Therefore, an object of the disclosure is to provide a surgery system, a contactless control panel for a surgery system, and a control method that can alleviate at least one of the drawbacks of the prior art.

According to one aspect of the disclosure, the surgery system includes a contactless control panel, an infrared camera, a computer and a display device. The contactless control panel includes a panel body that includes a plurality of control areas. The control areas are arranged in a predetermined pattern, and are coated with infrared reflective material to reflect infrared radiation upon the control areas. The infrared radiation thus reflected has wavelengths in a specific wavelength range. The infrared camera is configured to capture an infrared image of the control areas of the contactless control panel reflecting the infrared radiation so as to generate an image signal related to the infrared image. The computer is electrically connected to the infrared camera, and is configured to receive the image signal, to perform image recognition on the infrared image based on the image signal, to determine which one of the control areas is masked based on the predetermined pattern that is stored in the computer in advance and a result of the image recognition, and to generate a device control signal based on a function corresponding to the one of said control areas that is determined to be masked. The display device is electrically connected to the computer, and is configured to receive the device control signal, and to display images based on the device control signal.

According to another aspect of the disclosure, the contactless control panel includes a panel body. The panel body has a surface, and includes a plurality of control areas on the surface. The control areas are arranged in a predetermined pattern, and are coated with infrared reflective material to reflect infrared radiation upon the control areas. The infrared radiation thus reflected has wavelengths in a specific wavelength range.

According to still another aspect of the disclosure, the control method is adapted to be implemented by the surgery system as previously described. The computer stores in advance the predetermined pattern, and a plurality of labels describing functions that respectively correspond to the control areas arranged in the predetermined pattern. The method includes steps of:

continuously capturing, by the infrared camera, multiple instances of an infrared image of the control areas of the contactless control panel reflecting the infrared radiation so as to generate an image signal related to the instances of the infrared image;

by the computer, receiving the image signal, performing image recognition on one of the instances of the infrared image based on the image signal, and controlling, based on a result of the image recognition, and the predetermined pattern and the labels stored in computer, the display device to display the labels at positions respectively corresponding to the control areas of the contactless control panel; and by the computer, performing image recognition on another one of the instances of the infrared image based on the image signal, determining, based on the predetermined pattern that is stored in the computer and a result of the image recognition, which one of the control areas is masked, and generating a device control signal based on the function corresponding to the one of the control areas that is determined to be masked; and by the display device, receiving the device control signal, and displaying images based on the device control signal.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
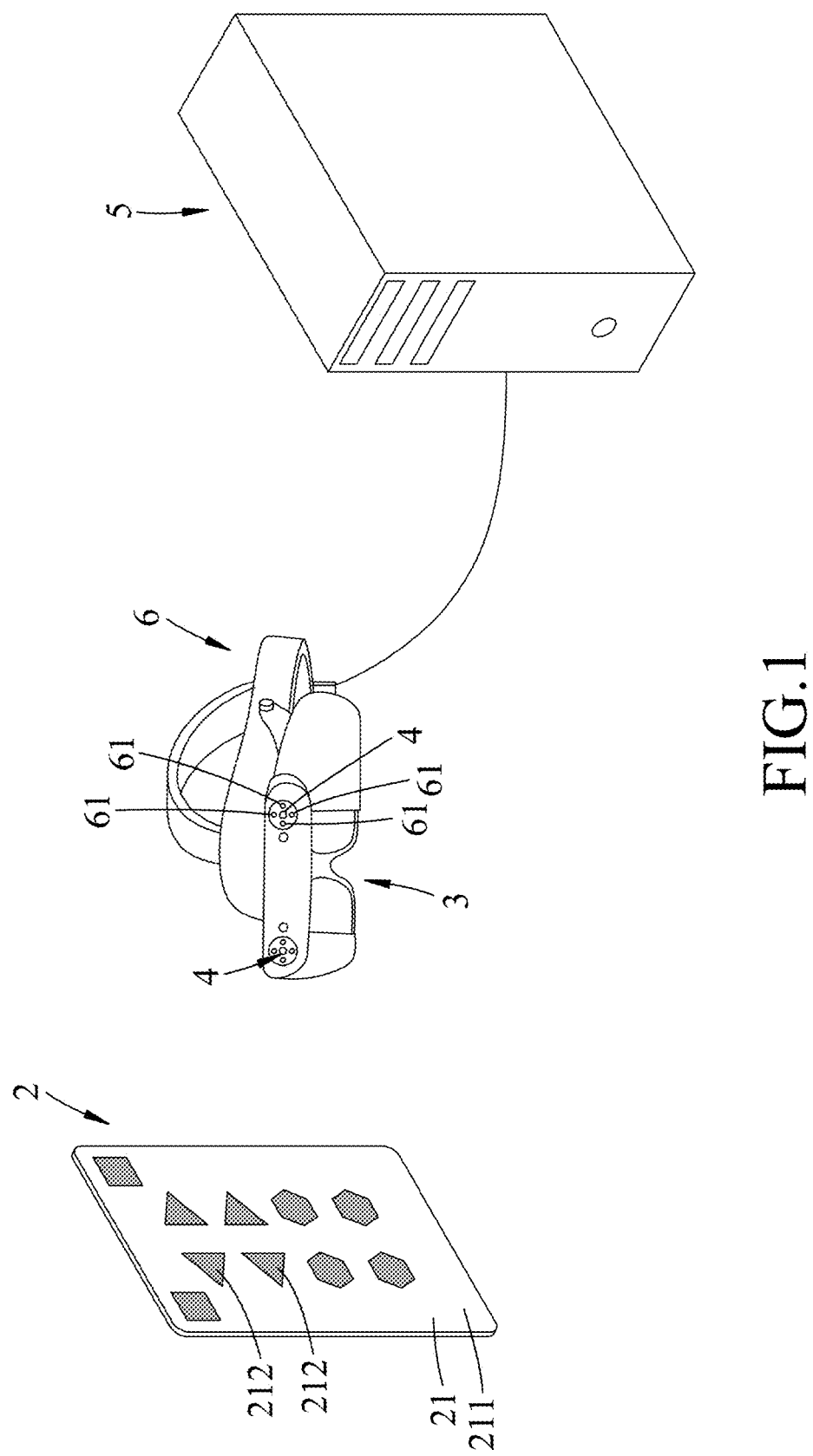
FIG. 1 is a perspective schematic diagram illustrating an embodiment of a surgery system according to the disclosure.
Figure 2:
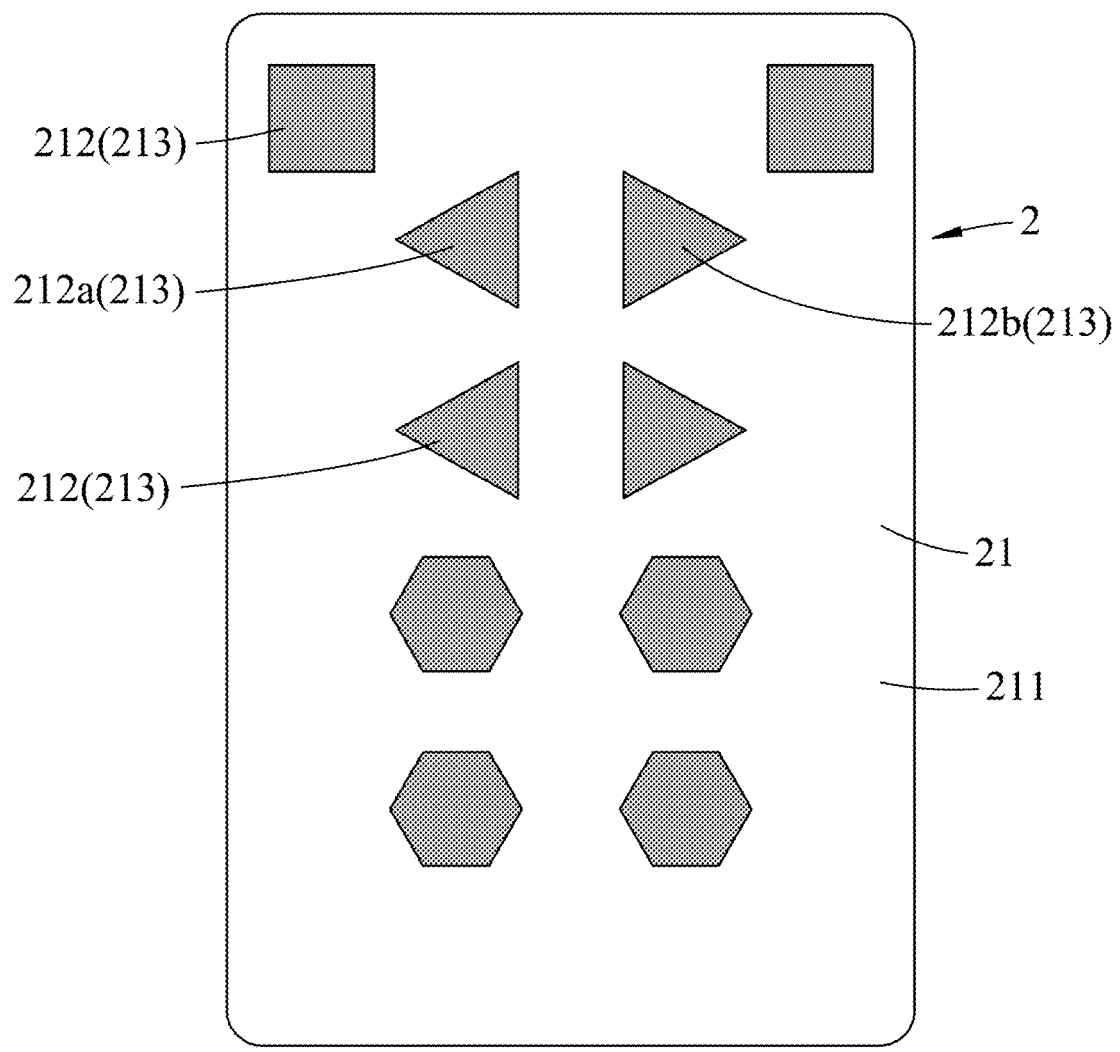
FIG. 2 is a front view illustrating an embodiment of a contactless control panel according to the disclosure.

Referring to FIGS. 1 and 2, an embodiment of a surgery system according to the disclosure is illustrated. The surgery system includes a contactless control panel 2, a display device 3, an infrared camera 4 and a computer 5.

The contactless control panel 2 includes a panel body 21. The panel body 21 has a surface 211, and includes a plurality of control areas 212 on the surface 211. The control areas 212 are arranged in a predetermined pattern, and are coated with infrared reflective material 213 to reflect infrared radiation upon the control areas 212. The infrared radiation thus reflected has wavelengths in a specific wavelength range.

Each of the control areas 212 has a shape of one of a triangle, a quadrilateral, a pentagon, a hexagon, and any combination thereof. As shown in FIG. 2, the predetermined pattern is composed of two quadrilaterals at the top, four triangles in the middle, and four hexagons at the bottom. However, the number, the positions and the shapes of the control areas 212 may vary according to different needs in practice, and are not limited to the disclosure herein.

The specific wavelength range is between 730 nanometers and 1100 nanometers. To prevent from interference caused by halogen light emitted by halogen lamps in an operating room, the specific wavelength range is between 750 nanometers and 950 nanometers in this embodiment.

In this embodiment, the panel body 21 is in the form of a tablet, is substantially rectangular in shape, and is lightweight. However, the form or shape of the panel body 21 is not limited to the disclosure herein and may vary in other embodiments. For example, the panel body 21 may be cylindrical, arc-shaped, columnar, or any shape, as long as there is a surface 211 for arrangement of the control areas 212. In this embodiment, the control areas 212 are defined simply by coating specific areas on the surface 211 with the infrared reflective material 213, i.e., the control areas 212 and the surface 211 are coplanar. However, the control areas 212 may slightly protrude from the surface 211 in other embodiments.

It is worth to note that the contactless control panel 2 does not include any electronic component. Therefore, the panel body 21 may be entirely made of plastic, or any material that can be sterilized. Additionally, the contactless control panel 2 may be disposable, reducing the risk of pathogen transmission.

The display device 3 is electrically connected to the computer 5. The display device 3 is configured to receive a device control signal, and to display images based on the device control signal. The display device 3 may be implemented by a monitor of a surgical navigation system (not shown), or a see-through display of a pair of head-mounted smartglasses 6 as shown in FIG. 1.

The infrared camera 4 is electrically connected to the computer 5. The infrared camera 4 is configured to capture an infrared image of the control areas 212 of the contactless control panel 2 reflecting infrared radiation so as to generate an image signal related to the infrared image. The infrared camera 4 may be implemented by a built-in infrared camera of the surgical navigation system or of the head-mounted smartglasses 6, but is not limited thereto. In one embodiment, the infrared camera 4 is adapted to be used together with at least one optical filter such that the infrared image captured by the infrared camera 4 is related to infrared radiation with wavelengths ranging between 840 nanometers and 860 nanometers. The optical filter may be one of a band-pass filter, a matched pair of a high-pass filter and a low-pass filter, and any combination thereof. It should be noted that the number of the infrared camera 4 is not limited to one, and may be plural according to actual needs.

The computer 5 is configured to store in advance the predetermined pattern and a plurality of labels. Each of the labels describes a function corresponding to a respective one of the control areas 212, which are arranged in the predetermined pattern. In one embodiment, the computer 5 also stores positions of the labels, which correspond to positions of the respective control areas 212. The computer 5 is communicable with the display device 3 and the infrared camera 4. The computer 5 is configured to receive the image signal, and to perform image recognition on the infrared image based on the image signal. Thereafter, the computer 5 is configured to determine, based on the predetermined pattern that is stored in the computer 5 and a result of the image recognition, which one of said control areas 212 is masked, and to generate the device control signal based on the function corresponding to the one of the control areas 212 that is determined to be masked.

In this embodiment, the display device 3, the infrared camera 4 and the computer 5 are realized by a product named "Caduceus—smart surgical glasses navigation system", which is developed by Taiwan Main Orthopaedics Biotechnology Co., Ltd., or another product that comes with functionalities of infrared image capturing, image processing and image displaying.

Figure 3:
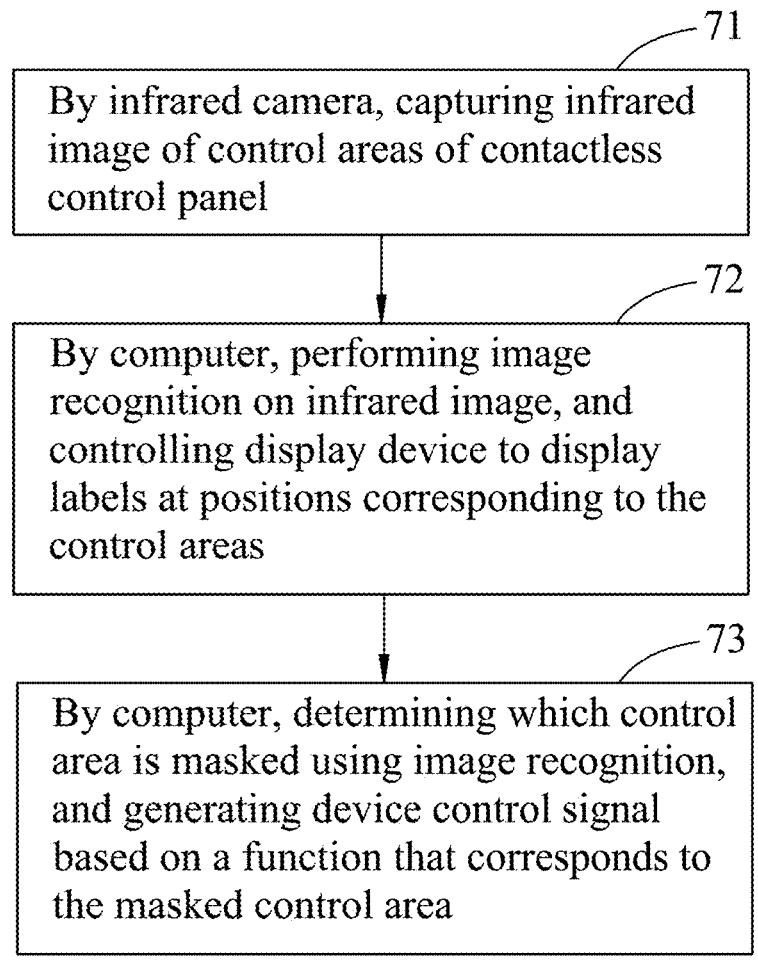
FIG. 3 is a flow chart illustrating an embodiment of a control method according to the disclosure.

Referring to FIGS. 1 to 3, an embodiment of a control method according to the disclosure is illustrated. The control method is adapted to be implemented by the surgery system as previously described. The method includes steps 71 to 73 outlined below.

In step 71, the infrared camera 4 continuously captures multiple instances of the infrared image of the control areas 212 of the contactless control panel 2 reflecting infrared radiation, so as to generate the image signal related to the instances of the infrared image.

In step 72, the computer 5 continuously receives the image signal, and performs image recognition on one instance of the infrared image based on the image signal. Subsequently, based on a result of the image recognition on the instance of the infrared image, and the predetermined pattern and the labels stored in the computer 5, the computer 5 controls the display device 3 to display the labels at positions respectively corresponding to the control areas 212 of the contactless control panel 2.

It should be noted that the result of the image recognition performed in step 72 is a recognized pattern that reflects an arrangement of the control areas 212 captured in the infrared image. Following the image recognition, the computer 5 determines whether the recognized pattern matches the predetermined pattern. When it is determined that the recognized pattern matches the predetermined pattern, the computer 5 controls the display device 3 to display the labels.

In this way, a surgeon wearing the head-mounted smartglasses 6 (see FIG. 1) is able to read the labels displayed by the display device 3 and know the functions corresponding to the control areas 212 of the contactless control panel 2, facilitating subsequent control inputs to the surgery system by the surgeon.

In step 73, the computer 5 performs image recognition on another instance of the infrared image based on the image signal, wherein the another instance of the infrared image is succeeding in time than the one instance of the infrared image. Based on the predetermined pattern that is stored in the computer 5 and a result of the image recognition on the another instance of the infrared image, the computer 5 determines which one of the control areas 212 is masked. Then, the computer 5 generates the device control signal based on the function corresponding to the one of the control areas 212 that is determined to be masked.

It should be noted that the result of the image recognition performed in step 73 is another recognized pattern which reflects the arrangement of the control areas 212 in the infrared image at another time, and the another recognized pattern would be incomplete compared to the recognized pattern obtained in step 72 because one of the control areas 212 is masked by the surgeon. The determination made in step 73 is related to comparison between the another recognized pattern and the predetermined pattern so as to find out which one of the control areas 212 is masked.

If the function corresponding to the masked one of the control areas 212 relates to image-displaying by the display device 3, the device control signal generated by the computer 5 may, for example, be an image data signal, and the computer 5 would transmit the device control signal to the display device 3, such that the display device 3 receives the device control signal, and displays images based on the device control signal.

In a scenario where the computer 5 stores data of computed tomography (CT) in advance and where one of the control areas 212 corresponds to a function of displaying CT images, when this particular control area 212 is determined to be masked, based on the data of CT and the function corresponding to the control area 212, the computer 5 would generate the device control signal which is related to displaying of CT images (for example, the signal may contain the data of CT) and transmit the generated device control signal to the display device 3, which would then display the CT images based on such device control signal. In other embodiments, the computer 5 may store in advance data of X-ray imaging, neuroimaging, or angiography, or any other image data related to images to be viewed during surgery, and in such case, some control areas 212 may correspond to functions of displaying X-ray images, displaying neuroimaging images, and displaying angiography images, etc.

In practice, the contactless control panel 2 has to be sterilized before being used during surgery. After undergoing the sterilizing process, the contactless control panel 2 may be packed in an aseptic pack through aseptic packaging. During surgery, an assistant would open the aseptic pack, take out the contactless control panel 2, and hand over the contactless control panel 2 directly to the surgeon or put the contactless control panel 2 at a suitable location. Subsequently, the surgeon may operate a variety of medical equipments via the surgery system according to the disclosure (e.g., turn on/off a surgical lamp, select one of the CT images, or operate an image-guided navigation system with the aid of the contactless control panel 2 serving as a virtual keyboard through augmented reality to control zoom in/out, change pages or move to the right/left side of image). Specifically speaking, these operations of medical equipments may be conducted by utilizing the infrared camera 4 to capture the infrared image of the control areas 212 of the contactless control panel 2 in order for the computer 5 to perform image recognition on the infrared image and generate the device control signal, and by the computer 5 controlling corresponding medical equipments to perform the necessary operation (e.g., the computer 5 controlling the display device 3, which may be the monitor of the surgical navigation system or the see-through display of the head-mounted smartglasses 6, to provide images to the surgeon based on the device control signal). Referring to FIG. 1 for further explanation, the see-through display (i.e., the lens part) of the head-mounted smartglasses 6 serves as the display device 3. On a front side of the head-mounted smartglasses 6, two infrared cameras 4 are respectively mounted on a left side and a right side. With respect to each of the infrared cameras 4, four infrared light-emitting diodes (LEDs) 61 are mounted on the front side and surround the infrared camera 4. The infrared LEDs 61 serve as a light source of the infrared radiation to be reflected by the control areas 212 of the contactless control panel 2 and to be captured by the infrared cameras 4. Specifically speaking, at least one of the infrared cameras 4 captures an infrared image of the control areas 212 of the contactless control panel 2 so as to output to the computer 5 the image signal that is related to the infrared image. The computer 5 performs image recognition on the infrared image based on the image signal. After obtaining the recognized pattern that reflects the arrangement of the control areas 212 in the infrared image and determining that the recognized pattern matches the predetermined pattern, the computer 5 activates the functionality of contactless control of the surgery system and controls the display device 3 to display the labels at positions respectively corresponding to the control areas 212 of the contactless control panel 2. When one of the control areas 212 is masked by the surgeon with a hand or an object, the computer 5 is able to determine, through performing image recognition on the infrared image captured by the infrared camera 4 once again and performing image comparison, that the one of the control areas 212 is masked, and then output the device control signal that is related to the function corresponding to the one of the control areas 212 that is masked.

For example, referring to the contactless control panel 2 shown in FIG. 2, two control areas 212a, 212b are respectively a left-pointing triangle and a right-pointing triangle, and respectively correspond to functions of toggling to a previous screen and toggling to a next screen. When the control area 212a is masked by a surgeon's hand between the infrared cameras 4 and the contactless control panel 2, the computer 5 performs image recognition on the infrared image captured by at least one of the infrared cameras 4, and determines that the control area 212a is masked by comparing the predetermined pattern and the result of the image recognition. Subsequently, the computer 5 outputs the device control signal, which contains contents of a previous screen, to the display device 3 so as to control the display device 3 to toggle to the previous screen. Likewise, when the control area 212b is masked by the surgeon's hand between the infrared cameras 4 and the contactless control panel 2, the computer 5 performs image recognition on the infrared image captured by at least one of the infrared cameras 4, and determines that the control area 212b is masked by comparing the predetermined pattern and the result of the image recognition. Subsequently, the computer 5 outputs the device control signal, which contains contents of a next screen, to the display device 3 so as to control the display device 3 to toggle to the next screen. In this way, the surgeon is able to operate the surgery system according to the disclosure without touching the contactless control panel 2.

It is worth noting that in order to realize control of a medical equipment such as a surgical lamp, the surgery system according to the disclosure controls the display device 3 to display the labels over the contactless control panel 2 to realize a virtual keyboard for a surgeon. After that, the surgeon can operate the surgery system according to the disclosure by masking one of the control areas 212 of the contactless control panel 2 which serves as the virtual keyboard. Based on a result of image recognition performed on the infrared image of the control areas 212 of the contactless control panel 2, the computer 5 outputs the device control signal (e.g., signals complying with the RS-232 standard) to the medical equipment (e.g., the surgical lamp) over a communication network via RJ45 connectors. In this way, control of the medical equipment such as turning the surgical lamp on/off or adjusting brightness of light emitted by the surgical lamp can be realized through the surgery system according to the disclosure.

It is worth to note that the functions corresponding respectively to the control areas 212 may relate to turning on/off the display device 3, zooming in/out an image displayed by the display device 3, adjusting image contrast of an image displayed by the display device 3, mirroring images displayed by the display device 3, controlling the display device 3 to display personal information of a patient, controlling the display device 3 to display a control menu of a medical equipment that is associated with a vendor name, a usage description and/or size information, making a phone call, controlling voice volume in the phone call, ending the phone call, or making a direct-dial phone call.

In summary, the surgery system and the control method according to the disclosure utilizes the infrared camera(s) 4 to capture an infrared image of the control areas 212 of the contactless control panel 2, and utilizes the computer 5 to perform image recognition on the infrared image and to carry out a corresponding control operation based on the result of the image recognition. Since the surgeon does not have to touch the contactless control panel 2 and the contactless control panel 2 may be disposable, the risk of pathogen transmission may consequently be reduced. Moreover, with the aid of the contactless control panel 2, the surgeon is able to operate the surgery system according to the disclosure by himself/herself without worrying that the surgery system may be contaminated due to human contact, and the surgery may be carried out smoothly. In addition, not including any electronic component, the contactless control panel 2 may be sterilized without worrying about damaging any electronic component therein which may lead to malfunctioning of the contactless control panel 2. Furthermore, the contactless control panel 2 may be simply made by coating specific areas on a plastic board with the infrared reflective material 213, reducing both complexity of the manufacturing process and production cost of the contactless control panel 2.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A surgery system, comprising:
   a contactless control panel including a panel body that includes a plurality of control areas, said control areas being arranged in a predetermined pattern, and being coated with infrared reflective material to reflect infrared radiation upon said control areas, the infrared radiation thus reflected having wavelengths in a specific wavelength range;
   an infrared camera configured to capture an infrared image of said control areas of said contactless control panel reflecting the infrared radiation so as to generate an image signal related to the infrared image;
   a computer electrically connected to said infrared camera, and configured to receive the image signal, to perform image recognition on the infrared image based on the image signal, to determine which one of said control areas is masked based on the predetermined pattern that is stored in said computer in advance and a result of the image recognition, and to generate a device control signal based on a function corresponding to the one of said control areas that is determined to be masked; and
   a display device electrically connected to said computer, and configured to receive the device control signal, and to display images based on the device control signal.

2. The surgery system as claimed in claim 1, wherein the specific wavelength range is between 730 nanometers and 1100 nanometers.

3. The surgery system as claimed in claim 1, wherein each of said control areas has a shape of one of a triangle, a quadrilateral, a pentagon, a hexagon, and any combination thereof.

4. The surgery system as claimed in claim 1, wherein said contactless control panel does not include any electronic component.

\* \* \* \* \*